US012245842B2

(12) United States Patent
Little

(10) Patent No.: US 12,245,842 B2
(45) Date of Patent: Mar. 11, 2025

(54) DETAINEE HEALTH ALERT DEVICE

(71) Applicant: The Johns Hopkins University, Baltimore, MD (US)

(72) Inventor: Malik R. Little, Glen Burnie, MD (US)

(73) Assignee: The Johns Hopkins University, Baltimore, MD (US)

( * ) Notice: Subject to any disclaimer, the term of this patent is extended or adjusted under 35 U.S.C. 154(b) by 627 days.

(21) Appl. No.: 17/477,785

(22) Filed: Sep. 17, 2021

(65) Prior Publication Data

US 2022/0287576 A1 Sep. 15, 2022

Related U.S. Application Data

(60) Provisional application No. 63/158,586, filed on Mar. 9, 2021.

(51) Int. Cl.
| | |
|---|---|
| *A61B 5/0205* | (2006.01) |
| *A61B 5/00* | (2006.01) |
| *A61B 5/024* | (2006.01) |
| *A61B 5/145* | (2006.01) |
| *G16H 50/30* | (2018.01) |

(52) U.S. Cl.
CPC ........ *A61B 5/02055* (2013.01); *A61B 5/0004* (2013.01); *A61B 5/024* (2013.01); *A61B 5/14532* (2013.01); *A61B 5/14542* (2013.01); *A61B 5/681* (2013.01); *A61B 5/7405* (2013.01); *A61B 5/746* (2013.01); *G16H 50/30* (2018.01); *A61B 2560/02* (2013.01)

(58) Field of Classification Search
CPC . A61B 5/02055; A61B 5/024; A61B 5/14542; A61B 5/681; A61B 5/7405; A61B 5/746; G16H 50/30

USPC ........................................................ 340/573.1
See application file for complete search history.

(56) References Cited

U.S. PATENT DOCUMENTS

| | | | |
|---|---|---|---|
| 8,839,796 B2 | 9/2014 | Reese et al. | |
| 10,002,635 B2 | 6/2018 | Mack et al. | |
| 10,458,154 B2 * | 10/2019 | Caprino | E05B 75/00 |
| 11,043,242 B2 | 6/2021 | Mack et al. | |
| 11,507,909 B2 | 11/2022 | Jones et al. | |
| 2003/0107487 A1 | 6/2003 | Korman et al. | |

(Continued)

FOREIGN PATENT DOCUMENTS

WO 2023003711 1/2023

*Primary Examiner* — Kam Wan Ma
(74) *Attorney, Agent, or Firm* — Noah J. Hayward

(57) ABSTRACT

A health alert device includes a physiological sensor and processing circuitry. The physiological sensor captures physiological data, including heart rate and blood oxygen data, of a detainee. The processing circuitry repeatedly receives the physiological data, calculates a health metric parameter based on a combination of the physiological data, determines a health metric baseline based on a series of health metric parameters determined over a baseline determination duration, determines first and second risk alert thresholds based on the health metric baseline, determines a health metric delta based on newly received physiological data and the health metric baseline, and transmits first and second risk alert communications to an alert device to cause the alert device to display first and second risk alerts on an alert device display in response to the health metric delta exceeding the first and second risk alert thresholds, respectively.

21 Claims, 10 Drawing Sheets

(56) References Cited

U.S. PATENT DOCUMENTS

| | | |
|---|---|---|
| 2014/0340217 A1 | 11/2014 | Moenning et al. |
| 2015/0230754 A1 | 8/2015 | Willis |
| 2018/0187455 A1 | 7/2018 | Livshits et al. |
| 2019/0183430 A1* | 6/2019 | Alphonse .............. A61B 5/1118 |
| 2021/0134455 A1 | 5/2021 | Smith |
| 2022/0207635 A1* | 6/2022 | Hughes .................. E05B 45/00 |
| 2022/0233119 A1* | 7/2022 | Shelton, IV ..... A61B 17/07207 |
| 2023/0013865 A1 | 1/2023 | Rebro |
| 2023/0141400 A1 | 5/2023 | Rebro |

\* cited by examiner

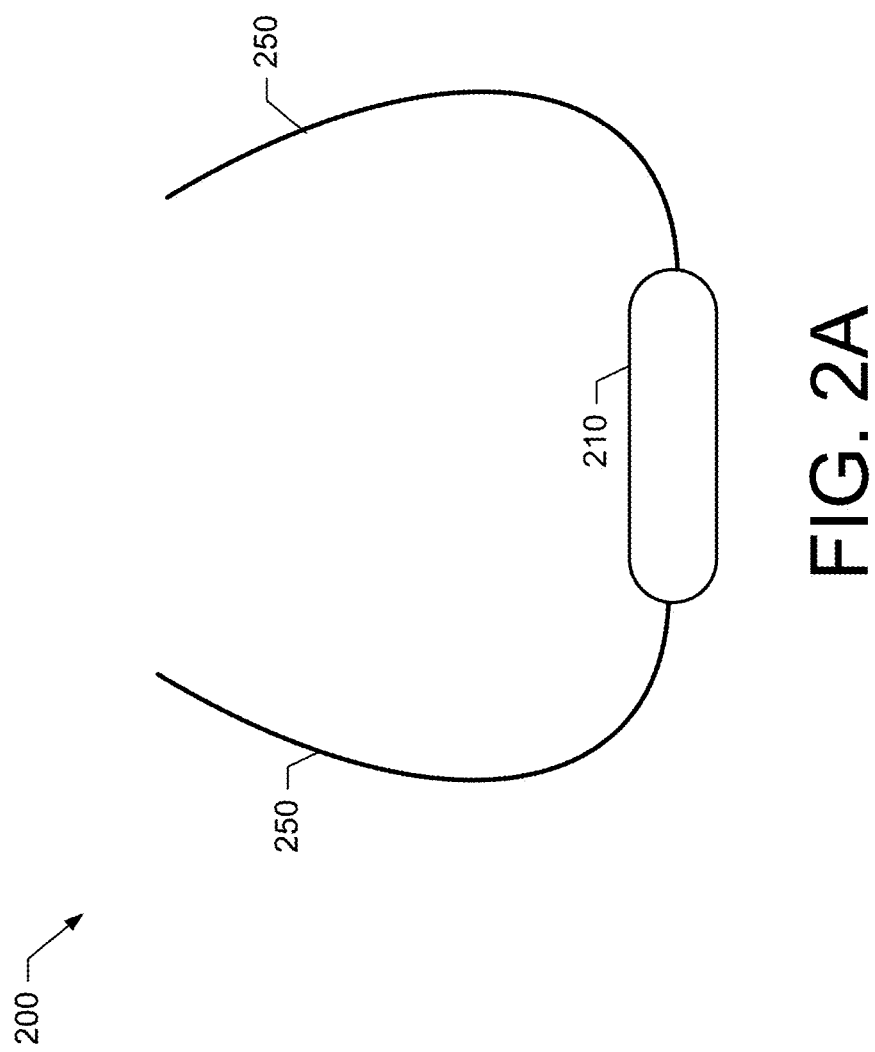

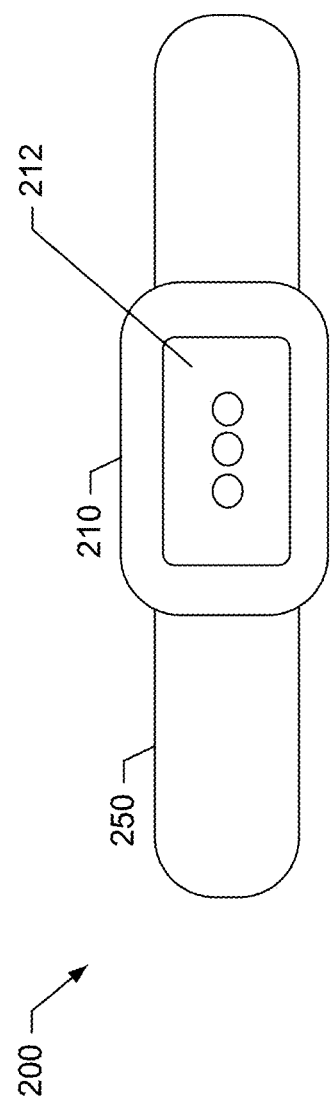
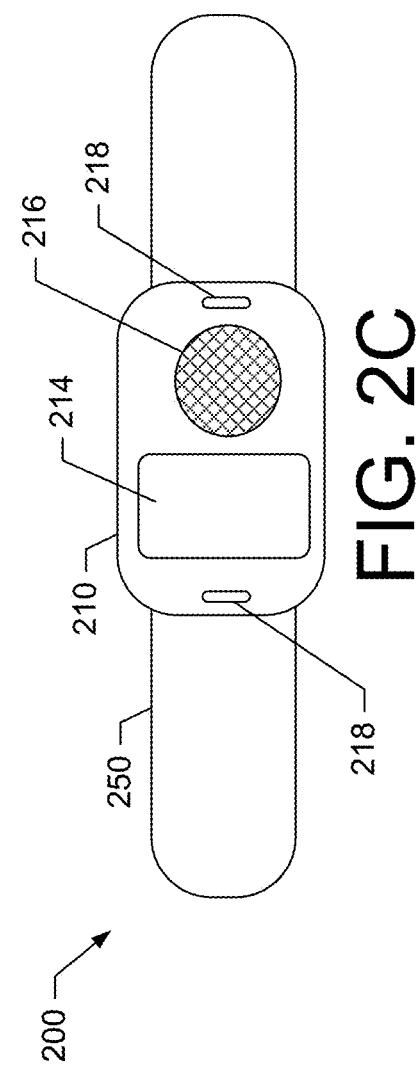

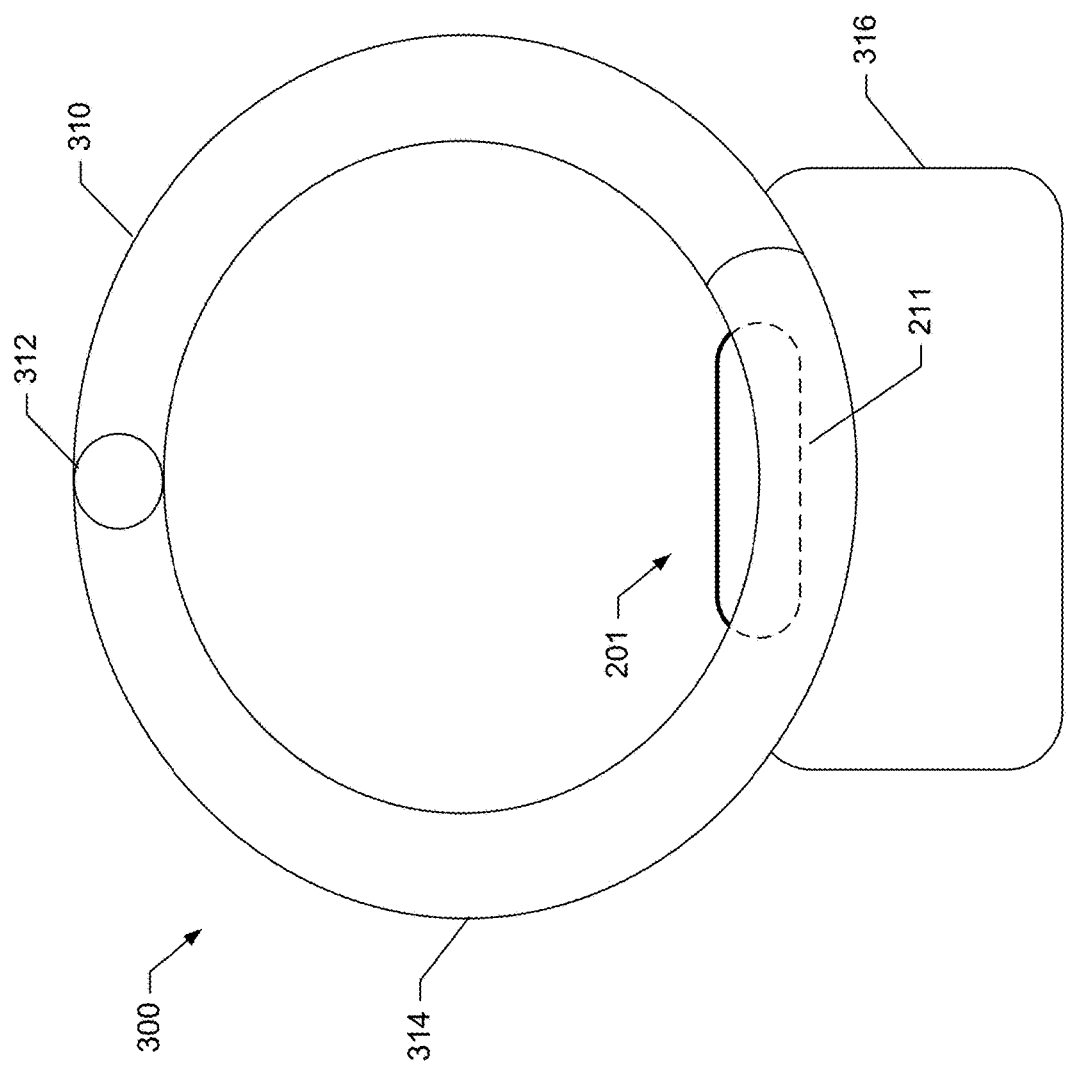

DETAINEE HEALTH ALERT DEVICE

CROSS-REFERENCE TO RELATED APPLICATIONS

This application claims priority to and the benefit of prior-filed, U.S. Provisional Application No. 63/158,586 filed on Mar. 9, 2021, the entire contents of which are hereby incorporated herein by reference.

TECHNICAL FIELD

Example embodiments generally relate to physiological sensors and monitoring systems and, in particular, relate to health-related risk alert systems for the protection of detainees.

BACKGROUND

The process of an individual being detained by law enforcement can result in significant effects on the detainee's biologic bodily systems. In many circumstances, the arrest process involves physical and physiological stress that can affect the individual's respiratory and cardiovascular systems. In some instances, the presence of drugs or alcohol in the detainee's system can exacerbate the impacts. The physiological effects of these and other factors on the detainee can have a spiraling effect where sudden changes can occur leading to illness in the form of, for example, hyperventilation creating a lack of oxygen in the blood, cardiac arrest, and even death.

In an effort to prevent such outcomes, arresting officers attempt to monitor the health of the arrested and detained individual by, for example, regularly talking to the detainee to determine lucidness. However, such checks on a detainee often do not reveal underlying changes that may be occurring in the detainee's physiology. Also, these interactions with the detainee can be ineffective when physiological changes occur more rapidly or when the arresting officer is forced to address other law enforcement-related issues that may be still occurring at the scene of an arrest.

Accordingly, there is a need for improvements to detect a detainee's change in physiology that might occur during an arrest and to assist arresting officers in monitoring and responding to changes in the health of a detained individual to prevent unintentional injury or potentially death during apprehension and detention.

BRIEF SUMMARY

According to some non-limiting, example embodiments, a system includes an alert device and a detainee health alert device. The alert device includes an alert device display. The detainee health alert device includes a physiological sensor, configured to capture physiological data of a detainee, and processing circuitry. The physiological data includes heart rate data and blood oxygen data. The processing circuitry is configured to repeatedly receive the physiological data from the physiological sensor, calculate a health metric parameter based on a combination of the heart rate data and blood oxygen data, determine a health metric baseline based on a series of health metric parameters determined over a baseline determination duration, determine a first risk alert threshold and a second risk alert threshold based on the health metric baseline, determine a health metric delta based on newly received physiological data and the health metric baseline, transmit a first risk alert communication to the alert device to cause the alert device to display a first risk alert on the alert device display in response to the health metric delta exceeding the first risk alert threshold, and transmit a second risk alert communication to the alert device to cause the alert device to display a second risk alert on the alert device display in response to the health metric delta exceeding the second risk alert threshold.

According to additional, non-limiting example embodiments, a detainee health alert device includes a physiological sensor, configured to capture physiological data of a detainee, and processing circuitry. The physiological data includes heart rate data and blood oxygen data. The processing circuitry is configured to repeatedly receive the physiological data from the physiological sensor, calculate a health metric parameter based on a combination of the heart rate data and blood oxygen data, determine a health metric baseline based on a series of health metric parameters determined over a baseline determination duration, determine a first risk alert threshold and a second risk alert threshold based on the health metric baseline, determine a health metric delta based on newly received physiological data from the physiological sensor and the health metric baseline, transmit a first risk alert communication to an alert device to cause the alert device to display a first risk alert on an alert device display in response to the health metric delta exceeding the first risk alert threshold, and transmit a second risk alert communication to the alert device to cause the alert device to display a second risk alert on the alert device display in response to the health metric delta exceeding the second risk alert threshold.

According to additional, non-limiting example embodiments, a method includes repeatedly receiving physiological data from a physiological sensor, the physiological data including heart rate data and blood oxygen data, calculating, by processing circuitry, a health metric parameter based on a combination of the heart rate data and blood oxygen data, determining, by the processing circuitry, a health metric baseline based on a series of health metric parameters determined over a baseline determination duration, determining, by the processing circuitry, a first risk alert threshold and a second risk alert threshold based on the health metric baseline, determining, by the processing circuitry, a health metric delta based on newly received physiological data from the physiological sensor and the health metric baseline, transmitting a first risk alert communication to an alert device to cause the alert device to display a first risk alert on an alert device display in response to the health metric delta exceeding the first risk alert threshold, and transmitting a second risk alert communication to the alert device to cause the alert device to display a second risk alert on the alert device display in response to the health metric delta exceeding the second risk alert threshold.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

FIGS. 2A-2C illustrate an example detainee health alert device according to some example embodiments;

FIGS. 3A and 3B illustrate detainee health alert devices in physical coupling with a restraint device according to some example embodiments;

DETAILED DESCRIPTION

Figure 1:
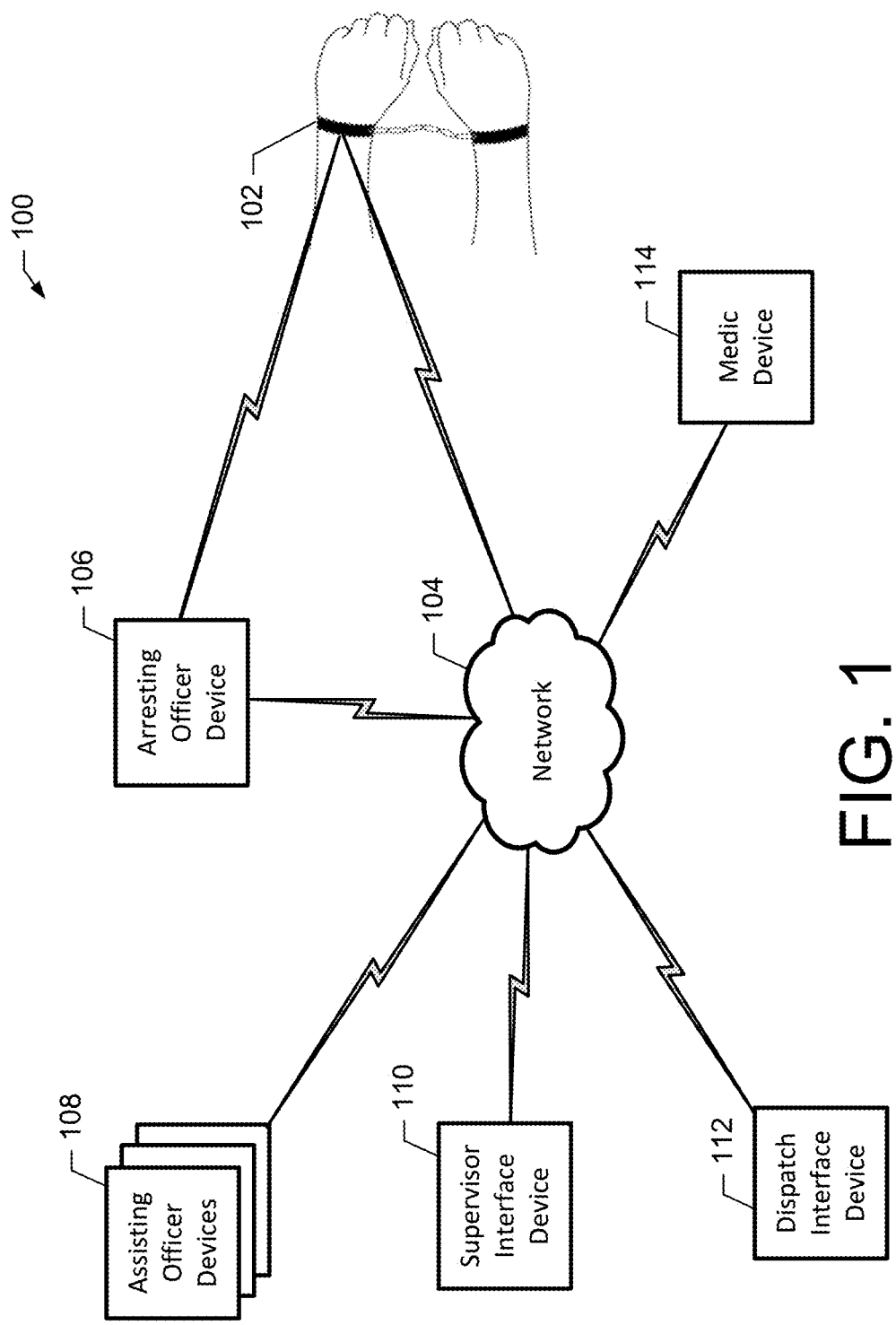
FIG. 1 illustrates an example system including a detainee health alert device according to some example embodiments.

Some non-limiting, example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, operable coupling should be understood to relate to direct or indirect connection that, in either case, enables functional interconnection of components that are operably coupled to each other.

According to various example embodiments, a detainee health alert device and associated systems and methods are provided. The detainee health alert device may be applied to a detainee, and physiological sensors of the detainee health alert device may capture physiological data about, for example, operation of a detainee's biological systems (e.g., respiratory, cardiovascular, etc.) for analysis to determine a health metric parameter for the detainee. Such physiological data may include, for example, heart rate, blood oxygen level, temperature, blood pressure, blood glucose level, and the like. The physiological sensors may be operably coupled to processing circuitry configured to analyze the physiological data to develop the health metric parameter and trigger alerts if the health metric parameter exceeds situationally-defined thresholds. Such alerts may include local alerts on a display of the detainee health alert device or via a sounder of the detainee health alert device. The triggering of alerts may also include transmission of a communication to a remote alert device, directly or via a network. The alert-triggered communication may cause the alert device to display a risk alert on a display of the alert device or cause the alert device to emit a sound via a sounder of the alert device. The alert device may be one in the possession of an arresting officer or assisting officers, a computer in a squad car, a computing device at dispatch location, medical facility, supervisor's office, or the like. Regardless of the type of alert that is triggered, the alert is provided to prompt arresting or assisting officers, medical personnel, or the like to take action with respect to the detainee's health because the detainee's health has declined as indicated by the health metric parameter.

According to some example embodiments, the detainee health alert device may be operably coupled to a restraint device that is applied to the individual being arrested. An example of such a restraint device may be hand cuffs. In this regard, the detainee health alert device may be affixed to (retrofit), or integrated into, the restraint device. With respect to a hand cuff implementation, the detainee health alert device may be positioned on the interior of the securing cuff to ensure contact between the detainee's wrist and the physiological sensor of the detainee health alert device. According to some example embodiments, the detainee health alert device may include spring-loaded clasps that, at least partially, wrap around the detainee's wrist to increase stable contact between the physiological sensor and the detainee's wrist.

According to some example embodiments, the detainee health alert device may be applied to the detainee's body separate from a restraint device. For example, the detainee health alert device may be applied as a physically separate clasping device, possibly using spring-loaded clasps, to the detainee's wrist, upper arm, ankle, thigh, finger, neck, etc. According to some example embodiments, the detainee health alert device may be applied in association with an adhesive patch that affixes the physiological sensor on the body of the detainee at the applied location.

Having provided a general overview of some aspects of example embodiments, FIG. 1 illustrates an example system 100. The system 100 includes a detainee health alert device 102, that is associated with handcuffs, and a number of alert devices that are remote from, but in communication with, the detainee health alert device 102 either directly or via a network 104. The various types of alert devices operating as network entities may include an arresting officer device 106, assisting officer devices 108, a supervisor interface device 110, a dispatch interface device 112, and a medic device 114. The alert devices may be include communications capabilities and a user interface to output visual or audible risk alerts, as well as other related-information.

The arresting officer device 106 and the assisting officer devices 108 may be smart phones or the like that are carried on the officer's person. As such, when these devices output a risk alert, the officers may be immediately aware of the alert and take action to rectify the health risk to the detainee. The supervisor interface device 110, the dispatch interface device 112, and the medic device 114 may be more remote devices that are likely to be communicated with via a network, such as the Internet. The supervisor interface device 110 and the dispatch interface device 112 may be monitoring interfaces that may be configured to monitor activity of a number of detainee health alert devices that may be deployed in the field. The medic device 114 may be, for example, installed in an ambulance or the like to provide a risk alert to medical personnel and prompt the medical personnel to move to the location of the detainee to provide medical services.

Now referring to FIGS. 2A-2C, an example detainee health alert device 200 will be described. According to some example embodiments, the detainee health alert device 200 may be structured and operate the same or similar to the detainee health alert device 102 described above. The detainee health alert device 200 may include a main housing 210 and clasps 250. The main housing 210 may hold various circuitry and components for implementing the functionalities of the detainee health alert device 200 as described herein. The clasps 250 may be configured to assist with securing the main housing 210 to a detainee's body, in this case the detainee's wrist. In this regard, the clasps 250 may be configured to secure the main housing 210 in a properly applied position on a detainee's wrist and have an adjustability feature to permit use of the detainee health alert device 200 on a variety of differently sized wrists. The clasps

250 may also be designed to allow for easy and quick application of the detainee health alert device 200 to a detainee, to avoid difficulties of applying the detainee health alert device 200 to an uncooperative detainee.

As such, the clasps 250 may take many forms. For example, the clasps 250 may be semi-rigid members that bias inward toward the detainee's wrist to secure the detainee health alert device 200 to the detainee. Alternatively, the clasps 250 may be elastic with a connecting feature at the ends of the clasps 250 to secure the clasps 250 completely around the detainee wrist. Alternatively, according to some example embodiments, the clasps 250 may be formed of steel or a similar metal elongated strips having a U-shaped cross-section that can quickly transition between a flat orientation and a curled orientation by buckling the strips when in the flat orientation (e.g., slap bracelet). As such, the clasps 250 may include a spring-bias or spring device that facilitates application of the detainee health alert device 200 on the individual being detained. According to some example embodiments, the clasps 250 need not completely surround the detainee's wrist, but may only partially surround the detainee's wrist, particularly in implementations that are coupled with a restraint device, as further described below.

Referring to FIG. 2B, a bottom view of the detainee health alert device 200 is provided. In this regard, the bottom may be the side of the detainee health alert device 200 that contacts the detainee's wrist. As such, the bottom side of the main housing 210 may include the physiological sensor 212. According to some example embodiments, the physiological sensor 212 may be a singular sensor configured to capture one or more forms of physiological data or a collection of sensors configured to capture one or more forms of physiological date. In this regard, the physiological sensor 212 may be configured to capture various physiological information about the detainee to which the detainee health alert device 200 is applied, including heart rate, blood oxygen level, temperature, blood pressure, blood glucose level, or the like. According to some example embodiments, the physiological sensor 212 may use a light source and a light receiver to detect some or all of the physiological data. In this regard, the light source may output light that is reflected off of the detainee's skin and the reflection may be received by the light receiver. The signal of the reflection, relative to the signal of the source light, may be analyzed to reveal physiological attributes such as a heartbeat or an amount of oxygen in the blood stream. This, and other information from the physiological sensor 212 may be collected as physiological data and provided to processing circuitry for analysis according to some example embodiments.

Referring to FIG. 2C, a top view of the detainee health alert device 200 is provided. The top of the detainee health alert device 200 may be the side of the detainee health alert device 200 that faces away from the detainee's wrist when applied. As such, the top side of the main housing 210 may include, for example, a display 214, a sounder 216, and clamp connectors 218. The display 214 may be, for example, a color display (such as a liquid crystal display (LCD)) that may be driven by processing circuitry to output information. In this regard, the display 214 may be configured to output risk alerts based on the physiological data captured by the physiological sensor 212. For example, based on a health condition of the detainee the display 214 may be controlled to output different colors, such as, green, yellow, or red. The colors provided on the display 214 may be used to prompt a response by, for example, an arresting officer. If the display 214 is controlled to output green, this may communicate that the physiological data does not indicate that a health risk is presenting for the detainee and no heightened health-related response by, for example, the arresting officer is needed. If the display 214 is controlled to output yellow (i.e., first risk alert), this may communicate that the physiological data indicates that a risk alert threshold has been reached, thereby prompting, for example, the arresting officer to modify the detainee's conditions in an effort to reduce the risk of a subsequent health event to the detainee. If the display 214 is controlled to output red (i.e., second risk alert), this may communicate that the physiological data indicates that a higher risk alert threshold has been reached, thereby prompting, for example, the arresting officer to take immediate measures to modify the detainee's conditions in an effort to reduce the risk of a subsequent health event to the detainee including, for example, contacting medical personnel.

The sounder 216 may be controlled to operate in similar manner to the display 214, albeit in an audible manner. In this regard, the sounder 216 may be any type of device that may be configured to controllably emit a sound, and, in some example embodiments, a plurality of different sounds. As such, the sounder 216 may be a speaker. The sounder 216 may be controlled by processing circuitry of the detainee health alert device 200. Following from the description above, the sounder 216 may be configured to output a first sound (or series of first sounds) in accordance with a first risk alert and a second sound (or series of second sounds) in accordance with a second risk alert.

The detainee health alert device 200 may also include clamp connectors 218. As further described below with regard to clamps 320 (FIG. 3A), the clamp connectors 218 may be configured to secure the main housing 210 to a clamp 320. The clamp connectors 218 may utilize a mechanical and/or magnet connection to clamps 320, which may be configured to allow for a quick release feature to separate the main housing 210 from the clamps 320. The clamp connecters 218 may offer the flexibility of using the detainee health alert device 200 in association with a pair of hand cuffs or as a stand-alone, separate device.

Figure 3A:
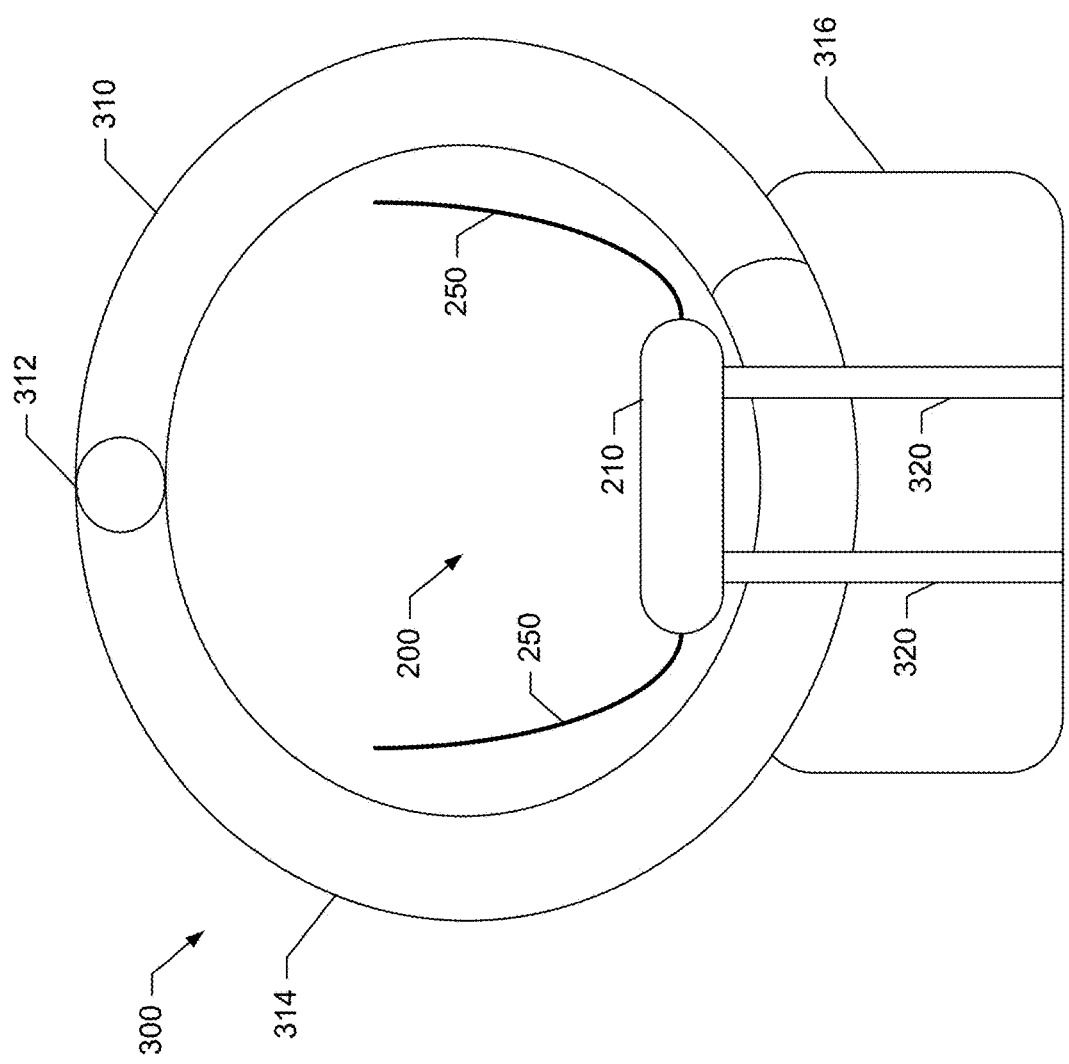

FIGS. 3A and 3B will now be described which illustrate a detainee health alert device in physical coupling with a restraint device according to some example embodiments. Specifically referring to FIG. 3A, an example implementation of the detainee health alert device 200 combined with a cuff 300 (e.g., a hand cuff 300) is shown. In this regard, the detainee health alert device 200 may be combined in a manner such that the detainee health alert device 200 may be retrofit onto conventional hand cuffs.

The cuff 300 may include a base arm 310 that is rigidly affixed to a base 316 of the cuff 300 and attached to a swivel arm 314 via a hinge 312. The swivel arm 314 may therefore be configured to swivel into an open position to permit a wrist to be received into the cuff 300. The swivel arm 314 may then be closed onto the wrist of the detainee and the swivel arm 314 may move into a locked engagement with the base arm 310 and the base 316. The swivel arm 314 may be further tightened in order to provide adjustability to the cuff 300.

The detainee health alert device 200 may be physically coupled to the cuff 300 via clamps 320. The clamps 320 may be affixed to the main housing 210 of the detainee health alert device 200 via the clamp connector 218 and may engage with the base 316 of the cuff 300 to secure the detainee health alert device 200 to the cuff 300. According to some example embodiments, clearance space for the main housing 210 may be provided to permit the swivel arm 314 to pass under the main housing 210 to be locked to the base 316 and the base arm 310. Additionally, according to some example embodiments, the main housing 210 may be detachably connected to the clamps 320 using a mechanical or magnetic connection.

With the detainee health alert device 200 physically coupled to the cuff 300, the clasps 250 may be positioned for application prior to application of the cuff 300 and the detainee health alert device 200 to the detainee. In this regard, the clasp 250 that is adjacent the swivel arm 314 may be moved into a flat position to permit the detainee's wrist to enter the cuff 300 and then after entry of the wrist, the clasp 250 may be adjusted to cause the clasps 250 to wrap around the detainee's wrist and cause the main housing 210 and the physiological sensor 212 to have stable contact with the detainee's wrist for obtaining physiological data.

Now referring to FIG. 3B, an integrated detainee health alert device 201 is shown in association with the cuff 300. In this regard, the detainee health alert device 201 may be structured and operate in the same or similar manner as the detainee health alert device 200, with the exception of including the clasps 250. However, it is noted that an integrated solution is contemplated that also incorporates the clasps 250.

A main housing 211 of the detainee health alert device 201 may be integrated into the base 316 of the cuff 300. To facilitate contact between the main housing 211 and the detainee's wrist, the main housing 211 may extend into the opening in the cuff 300 for receiving and securing the wrist. As such, the surface of the main housing 211 may contact the wrist to permit the physiological sensor to obtain physiological data for the detainee. According to some example embodiments, the main housing 211 may be spring biased to extend into the opening in the cuff 300 to ensure a stable engagement between the detainee's wrist and the physiological sensor.

Figure 4:
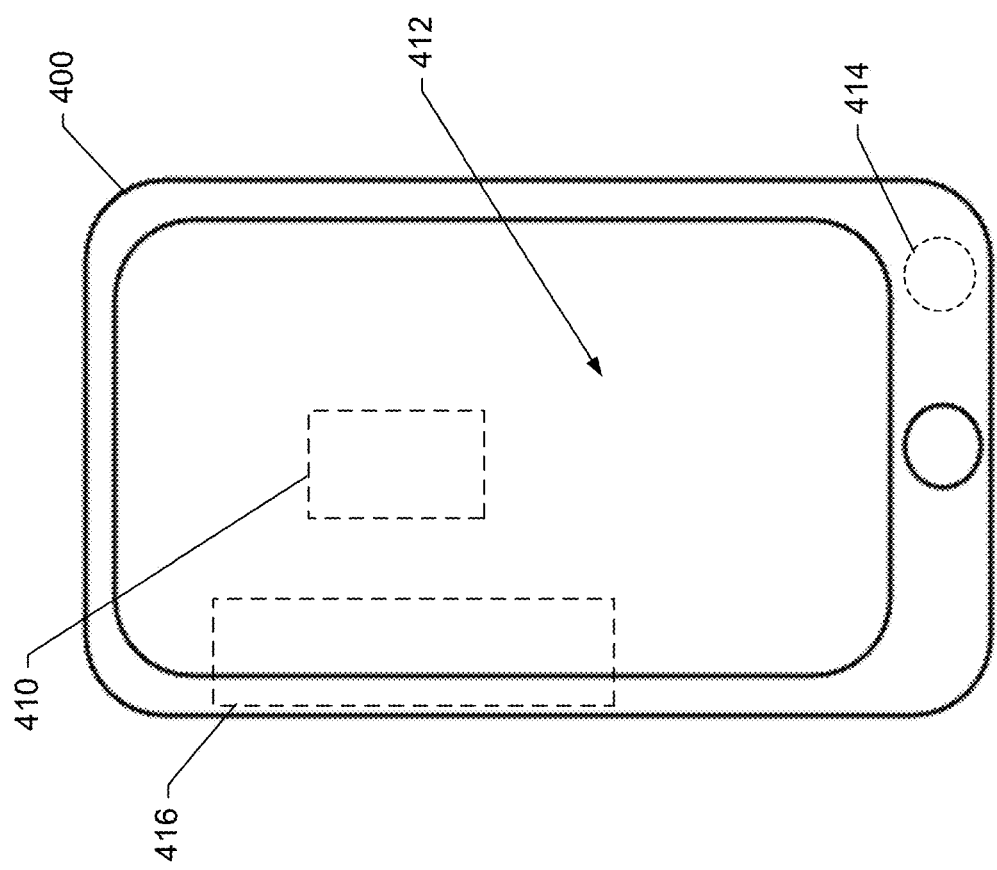
FIG. 4 illustrates an alert device according to some example embodiments.

Now referring to FIG. 4, example alert device 400 is shown. The alert device 400 may be any type of communications and processing device (e.g., smart phone, computer, etc.), mobile or non-mobile, embodied as the arresting officer device 106, the assisting officer devices 108, the supervisor interface device 110, the dispatch interface device 112, or the medic device 114. However, the example alert device 400 shown in FIG. 4 is in the form of a smart phone, which may, according to some example embodiments, be an example of an arresting officer device 106 or an assisting officer device 108.

The alert device 400 may include processing circuitry 410, an alert device display 412 (e.g., an LCD display), an alert device sounder 414, and an alert device communications interface 416. The processing circuitry 410 may be configured to control the operation of the alert device 400 to perform the functionalities described herein. In this regard, the processing circuitry 410 may be configured to control the alert device display 412 to display or render various visual outputs including risk alerts. In this regard, the alert device display 412 may be a color display capable of outputting different colors, including, for example, green, yellow, and red.

The alert device sounder 414 may be controlled by the processing circuitry 410 to provide an audible output. For example, the processing circuitry 410 may be configured to control the alert device sounder 414 to emit sounds or series of sounds as part of a risk alert. In this regard, the alert device sounder 414 may be configured to emit a first sound or a series of first sounds for a first risk alert and a second sound or a series of second sounds for a second risk alert.

Figure 5:
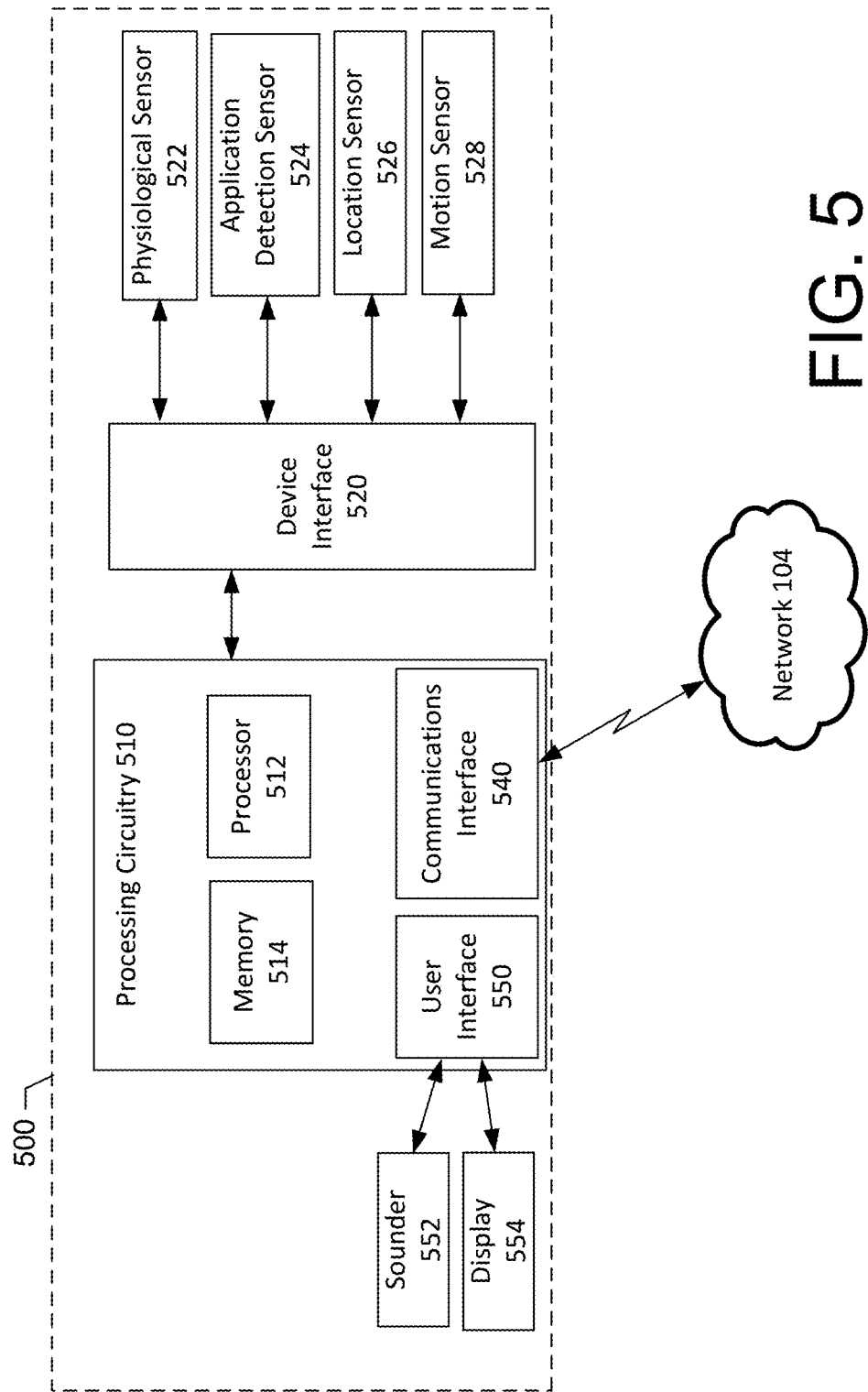
FIG. 5 is a block diagram of a detainee health alert device according to some example embodiments.

Now referring to FIG. 5, a block diagram of an example detainee health alert device 500 is shown. The detainee health alert device 500 may be structured and configured to operate in the same or similar manner as the detainee health alert device 200. Further, the configuration and functionalities of detainee health alert device 500 may also be implemented with the detainee health alert device 200. In this regard, the detainee health alert device 500 may include processing circuitry 510 and a device interface 520. Processing circuitry 510 may include a processor 512, a memory 514, a user interface 550, and a communications interface 540.

According to some example embodiments, processing circuitry 510 may be in operative communication with or embody, the memory 514, the processor 512, the user interface 550, and the communications interface 540. Through configuration and operation of the memory 514, the processor 512, the user interface 550, and the communications interface 540, the processing circuitry 510 may be configurable to perform various operations as described herein, including the operations and functionalities described with respect to a detainee health alert device. In this regard, the processing circuitry 510 may be configured to perform computational processing, memory management, user interface control and monitoring, and manage remote communications, according to some example embodiments. In some embodiments, the processing circuitry 510 may be embodied as a chip or chip set. In other words, the processing circuitry 510 may include one or more physical packages (e.g., chips) including materials, components or wires on a structural assembly (e.g., a baseboard). The processing circuitry 510 may be configured to receive inputs (e.g., via peripheral components such as the application detection sensor 524, the physiological sensor 522, and the location sensor 526), perform actions based on the inputs, and generate outputs (e.g., for provision to peripheral components such as the sounder 552 and the display 554). In an example embodiment, the processing circuitry 510 may include one or more instances of a processor 512, associated circuitry, and memory 514. As such, the processing circuitry 510 may be embodied as a circuit chip (e.g., an integrated circuit chip, such as a field programmable gate array (FPGA)) configured (e.g., with hardware, software or a combination of hardware and software) to perform operations described herein.

In an example embodiment, the memory 514 may include one or more non-transitory memory devices such as, for example, volatile or non-volatile memory that may be either fixed or removable. The memory 514 may be configured to store information, data, applications, instructions or the like for enabling, for example, the functionalities described with respect to a detainee health alert device. The memory 514 may operate to buffer instructions and data during operation of the processing circuitry 510 to support higher-level functionalities, and may also be configured to store instructions for execution by the processing circuitry 510. The memory 514 may also store various information including physiological data. According to some example embodiments, various data stored in the memory 514 may be generated based on other data and stored or the data may be retrieved via the communications interface 540 and stored in the memory 514.

As mentioned above, the processing circuitry 510 may be embodied in a number of different ways. For example, the processing circuitry 510 may be embodied as various processing means such as one or more processors 205 that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry 510 may be configured to execute instructions stored in the memory 514 or otherwise accessible to the processing circuitry 510. As such, whether configured by hardware or by a combination of hardware and software, the processing circuitry 510 may represent an entity (e.g., physically embodied in circuitry—in the form of processing circuitry 510) capable of performing operations according to example embodiments while configured accordingly. Thus, for example, when the processing circuitry 510 is embodied as an ASIC, FPGA, or the like, the processing circuitry 510 may be specifically configured hardware for conducting the operations described herein. Alternatively, as another example, when the processing circuitry 510 is embodied as an executor of software instructions, the instructions may specifically configure the processing circuitry 510 to perform the operations described herein.

The communications interface 540 may include one or more interface mechanisms for enabling communication with other devices external to the detainee health alert device 500, via, for example, network 104, which may, for example, be a local area network, the Internet, or the like, through a direct (wired or wireless) communication link to another external device, or the like. In some cases, the communications interface 540 may be any means such as a device or circuitry embodied in either hardware, or a combination of hardware and software that is configured to receive or transmit data from/to devices in communication with the processing circuitry 510. The communications interface 540 may be a wired or wireless interface and may support various communications protocols (WI-FI®, BLUETOOTH®, cellular, or the like).

The user interface 550 may be controlled by the processing circuitry 510 to interact with peripheral components or devices that can receive inputs from a user or provide outputs to a user. In this regard, via the user interface 550, the processing circuitry 510 may be configured to control output components such as, for example, a display 554, sounder 552, or the like. The user interface 550 may produce outputs, for example, as visual outputs on the display 554 that is local to the detainee health alert device 500, audio outputs via the sounder 552 that is local to the detainee health alert device 500, or the like.

The device interface 520 may be circuitry of the detainee health alert device 500 that may be embodied by the processing circuitry 510 or may be external to the processing circuitry 510 (as shown). The device interface 520 may be configured to interface with specialized components that perform specialized functionalities as described herein. Via the device interface 520, which in some instances, may include electrical connections between components and input and/or output ports of the processing circuitry 510, the processing circuitry 510 may interface with a physiological sensor 522, an application detection sensor 524, and a location sensor 526.

The physiological sensor 522 may be the same or similar to the physiological sensor 212. As such, the physiological sensor 522 may be embodied as one or more sensors configured to capture physiological data and provide the physiological data to the processing circuitry 510. The physiological data may include heart rate, blood oxygen level, temperature, blood pressure, blood glucose level, and the like. The processing circuitry 510 may be configured to control the operation of the physiological sensor 522 to place the physiological sensor 522 in an active or on state or in an inactive or off/dormant state (e.g., for battery conservation).

The application detection sensor 524 may be configured to detect application of the detainee health alert device 500 to a detainee and provide an applied signal as an output to the processing circuitry 510, from the application detection sensor 524. The application detection sensor 524 may take a number of different forms, however, in some example embodiments, the application detection sensor 524 may be a switch. In this regard, as a switch, the application detection sensor 524 may be physically coupled to the clasps 250 and mechanically actuated due to movement of the clasps 250. As such, the application detection sensor 524 may be configured to detect physical movement or a force being applied to the clasps 250 that would be indicative of the presence of a wrist, and therefore detect application of the detainee health alert device 500 to a detainee.

According to various example embodiments, the processing circuitry 510 may be configured to control the operation of the physiological sensor 522 based on receipt of the applied signal from the application detection sensor 524. According to some example embodiments, the processing circuitry 510 may be configured to maintain the physiological sensor 522 in a dormant state until the applied signal is received from the application detection sensor 524. In response to receiving the applied signal from the application detection sensor 524, the processing circuitry 510 may be configured to activate the physiological sensor 522 to begin capturing the physiological data.

With regard to the physiological data provided by the physiological sensor 522, the processing circuitry 510 may be configured to analyze the physiological data in a number of ways. As mentioned above, the physiological data may include a number of different types of physiological data, including heart rate, blood oxygen level, temperature, blood pressure, blood glucose level, and the like. According to some example embodiments, each type of physiological data may be compared to a standard value to determine if the physiological data indicates that a health event is increasingly likely to occur or is occurring. In this regard, according to some example embodiments, each type of physiological data may be applied to a respective threshold to determine whether a risk of a health event is more than a threshold amount. Additionally or alternatively, each of the types of physiological data that is captured (e.g., heart rate and blood oxygen level) may be combined to form a health metric parameter based on the respective data. For example, according to some example embodiments, a physiological sensor 522 may capture heart rate and blood oxygen level as the physiological data. These types of physiological data may be combined to form a health metric parameter. To combine the data of different types, each type of data (e.g., heart rate, blood oxygen level, etc.) may be normalized relative to a respective standard value for that type of data. For data that is improving with respect to health as the value increases (e.g., blood oxygen level), the value be negated prior to combination or, for example, the data may be converted prior to normalization by, for example, being subtracted from a set value (e.g., 100—blood oxygen level). Then the normalized versions of the data may be combined (e.g., added) to form the health metric parameter.

According to some example embodiments, the health metric parameter may be directly applied to risk alert thresholds to determine if a risk alert should be triggered. Alternatively, the health metric parameter may be determined as an average of, for example, the normalized and combined data, over time (e.g., using a moving average having a defined trailing time window), and this health metric parameter that is based on an average may be applied to risk alert thresholds to determine if a risk alert should be triggered. Additionally, as further described below, the health metric parameter that is averaged may be compared to a health metric baseline (as further described below) to determine a health metric delta, and the health metric delta may be compared to defined risk alert thresholds to determine if a risk alert should be triggered.

According to some example embodiments, the location sensor 526 may be circuitry configured to determine a current location of the detainee health alert device 500 and thus the detainee. This location feature may be useful for assisting medical personnel with locating the detainee if a medical event should occur. The location of the detainee health alert device 500 may be defined with respect to a coordinate system (e.g., latitude and longitude). The location sensor 526 may, for example, include circuitry (including for example antennas) configured to capture wireless signals that may be used for determining a location of the detainee health alert device 500 based on the signals. In this regard, the location sensor 526 may be configured to receive global positioning system (GPS) signals to determine a location of the detainee health alert device 500. Additionally or alternatively, the location sensor 526 may be configured to determine a position of the detainee health alert device 500 using locating techniques such as received signal strength, time of arrival, or the like.

According to some example embodiments, the detainee health alert device 500 may also include a motion sensor 528. Similar to the location sensor 526, the motion sensor 528 may be operably coupled to the processing circuitry 510 via the device interface 520. The motion sensor 528 may include an accelerometer, gyroscope, or the like to detect motion of the detainee health alert device 500 that may be applied to a detainee. According to some example embodiments, the motion sensor 528 may therefore collect motion information for provision to the processing circuitry 510. Based on the motion data, the processing circuitry 510 may be configured to assess the quality of the physiological data that is being obtained by the physiological sensor 522. For example, if movement is detected and the physiological sensor 522 ceases being able to detect physiological data, the processing circuitry 510 may be configured to determine that the movement caused the physiological sensor 522 to no longer be seated to properly collect physiological data. As such, for example, the processing circuitry 510 may be configured to sound an alarm via the sounder or send a missing data communication to an alert device indicating that physiological data is not being captured.

According to some example embodiments, the processing circuitry 510 may also be configured to consider or combine the motion data with the physiological data to determine the health metric parameter for the detainee. In this regard, the motion data may be analyzed to determine, for example, that the detainee is not stationary, but is in motion (e.g., walking, running, etc.). Accordingly, the motion status of the detainee may be considers when, for example, setting a health metric baseline and risk alert thresholds as further described below. For example, if the detainee is running or is otherwise in motion, the duration over which the health metric baseline is determined may be changed, such that the effect of the detainee running, and the associated effect on the physiological data, does not erroneously impact the setting of the health metric baseline due to, for example, an elevated heart rate. Further, according to some example embodiments, the health metric delta, as described below, may be determined based on the motion data, such that the effect of the detainee running, and the associated effect on the physiological data, does not erroneously impact the setting of the health metric delta due to, for example, an elevated heart rate.

Figure 6:
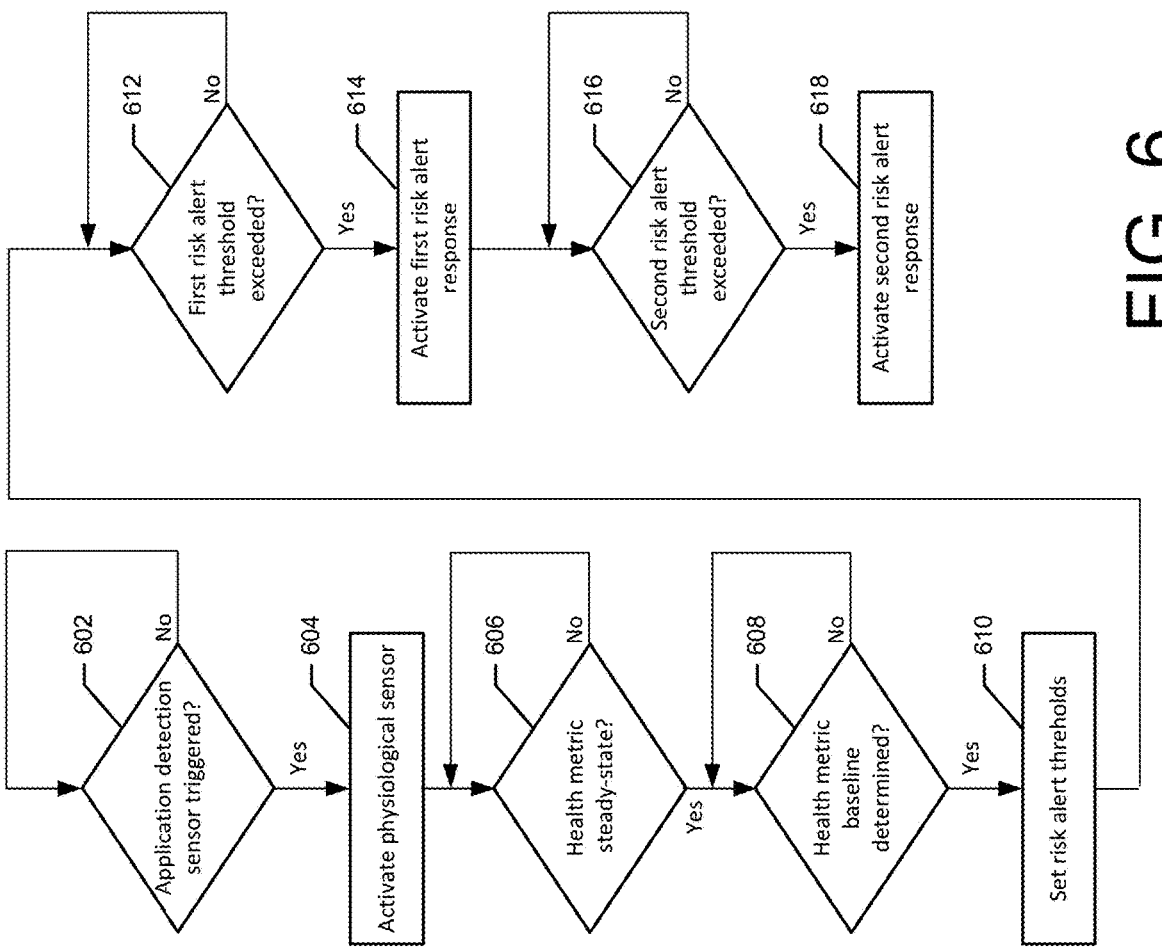
FIG. 6 is an operational flow chart for a detainee health alert device according to some example embodiments.
Figure 7:
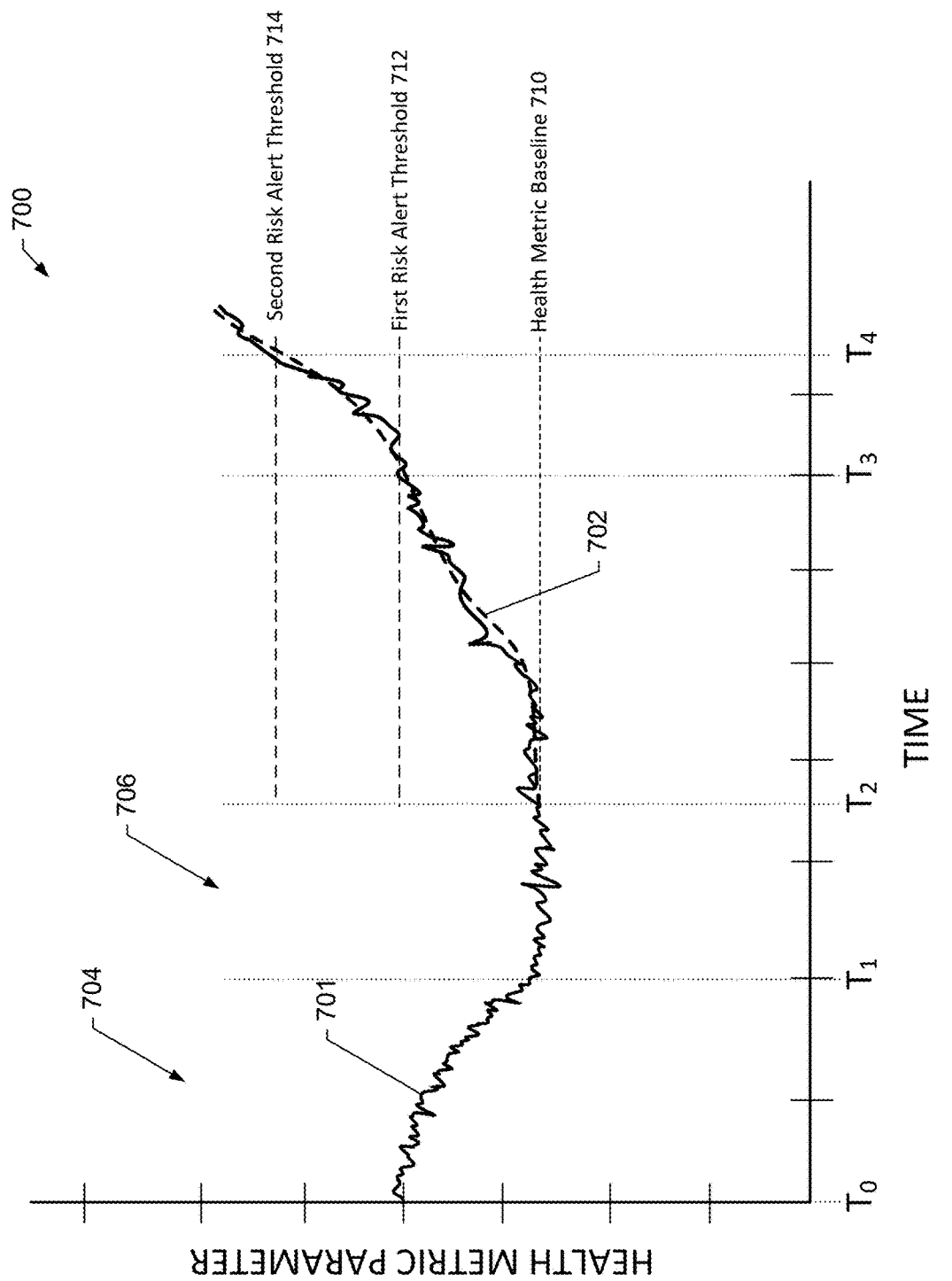
FIG. 7 is a graph of health metric parameters with respect to time according to some example embodiments.

Having described the components and configuration of the components of the detainee health alert device 500, the operational flow chart of FIG. 6 will now be described in association with the health metric parameter graph 700 of FIG. 7. In this regard, at 602, the processing circuitry 510 may be configured to determine if the application detection sensor 524 has be triggered based on whether the applied signal has been received from the application detection sensor 524. If the application detection sensor 524 has not been triggered (e.g., the applied signal has not been received by the processing circuitry 510), the processing circuitry 510 may continue to loop at 602 waiting for the application detection sensor 524 to be triggered. As described above, the processing circuitry 510 may be configured to activate the physiological sensor 522 at 604, when the applied signal is received by the processing circuitry 510 indicating that the application detection sensor 524 has been triggered and the detainee health alert device 500 has been applied to a detainee. Referring to the graph 700 of FIG. 7, the physiological sensor 522 may be activated at $T_0$, and begin capturing physiological data.

The processing circuitry 510 may then be configured to determine health metric parameters, at some defined time interval, based on the real-time, repeatedly received, physiological data from the physiological sensor 522. The processing circuitry 510 may be configured to determine if the health metric parameters have reached steady-state at 606. This concept of determining when the health metric parameter has reached steady-state may be necessary because, at the time the detainee health alert device 500 is applied to the detainee, the circumstances may be such that physiological data is not reliable for determining whether a risk alert should be triggered. This is because heightened physiological effects may occur immediately before application of a restraint device, due to the emotional stress of the arrest situation or a physical struggled that preceded the application of the restraint device. As such, the determination of whether the health metric parameter has reached steady-state after the detainee health alert device 500 has been applied may be determined in a variety of ways. According to some example embodiments, this determination may be made based on the passage of threshold amount of time (e.g., one minute). Alternatively, the health metric parameters that are being determined may be analyzed to determined when a slope of a series of health metric parameters is consistent (e.g., zero or near zero slope) relative to a certain health metric parameter value.

As such, after the health metric parameters begin to be determined at $T_0$, as indicated by the graph 701, a positive steady-state determination may be made at $T_1$. The time to steady-state between $T_0$ and $T_1$ on the graph 700 may be referred to as the time-to-steady-state duration 704. Subsequently, the processing circuitry 510 may be configured to determine if a health metric baseline has been determined at 608. In this regard, the processing circuitry 510 may be configured to determine a health metric baseline to be used for later analyses in a number of ways. In this regard, since the health metric parameter values have reached steady-state, after a further period of time, an average of the health metric parameters over that period time may be determined, and that average may be used as the health metric baseline 710. According to some example embodiments, the window of time over which the health metric baseline 710 is determined, also referred to as the baseline determination duration, may be a static duration (e.g. one minute) or a dynamic duration. For a dynamic duration, the health metric parameters may be analyzed during the averaging process and if a calculated average is not within a standard deviation threshold, then the averaging may continue until the average is within the standard deviation threshold.

Accordingly, the baseline determination duration 706 on graph 700 is the time from $T_1$ to $T_2$. As such, at $T_2$, the health metric baseline 710 may be defined by the processing circuitry 510. Subsequently, at 610, the processing circuitry 510 may be configured to determine and set risk alert thresholds based on the health metric baseline 710. Any number of risk alert thresholds may be defined. However, according to some example embodiments, two risk alert thresholds may be defined as a first risk alert threshold 712 and a second risk alert threshold 714. The values of the risk alert thresholds may be defined based on the value of the health metric baseline 710. In this regard, based on statistical analysis of data, predetermined percentage threshold differences may be used to define the risk alert thresholds. For example, the first risk alert threshold 712 may be set at 5% above the health metric baseline 710 or at 105% of the of the health metric baseline 710. Similarly, the second risk alert threshold 714 may be set at 10% above the health metric baseline 710 or 110% of the health metric baseline 710.

As such, with the risk alert thresholds set, the processing circuitry 510 may be configured to determine if the first risk alert threshold 712 is exceeded at 612. To determine if the first risk alert threshold 712 has been exceeded, the processing circuitry 510 may be configured to determine a health metric delta and compare the health metric delta to the risk alert thresholds. To determine the health metric delta, according to some example embodiments, an average of the health metric parameters 702 may be determined and a difference between the average and the health metric baseline 710 may be taken. This difference may be the health metric delta, which may be compared to the first risk alert threshold 712 (e.g., 5%).

If the health metric delta does not exceed to the first risk alert threshold 712, a satisfactory state may be determined. In the satisfactory state, the processing circuitry 510 may be configured to control the user interface 550 to have the display 554 and/or the sounder 552 to output a satisfactory alert. According to some example embodiments, the processing circuitry 510 may be configured to control the display 554 to output a green color and/or the sounder 552 to output a periodic tone at a relatively low frequency. Additionally, the processing circuitry 510 may control the communications interface 540 to transmit a satisfactory alert communication to the communication interface 416 of the alert device 400 to cause the processing circuitry 410 to control the alert device display 412 and/or the sounder 414 to output a satisfactory alert. According to some example embodiments, the processing circuitry 410 may be configured to implement the satisfactory alert by controlling the alert device display 412 to output a green color and/or the sounder 414 to output a periodic tone at a relatively low frequency.

However, if the health metric delta exceeds the first risk alert threshold 712, as indicated at $T_3$, a first risk state may be determined and the processing circuitry 510 may be configured to activate a first risk alert response at 614. In this regard, the processing circuitry 510 may be configured to control the user interface 550 to have the display 554 and/or the sounder 552 to output a first risk alert. According to some example embodiments, the processing circuitry 510 may be configured to control the display 554 to output a yellow color and/or the sounder 552 to output a periodic tone at a relatively moderate frequency (i.e., higher than the relatively low frequency for the satisfactory alert). Additionally, the processing circuitry 510 may control the communications interface 540 to transmit a first risk alert communication to the communication interface 416 of the alert device 400 to cause the processing circuitry 410 to control the alert device display 412 and/or the sounder 414 to output a first risk alert. According to some example embodiments, the processing circuitry 410 may be configured to implement the first risk alert by controlling the alert device display 412 to output a yellow color and/or the sounder 414 to output a periodic tone at a relatively moderate frequency (i.e., higher than the relatively low frequency for the satisfactory alert).

At 616, the processing circuitry 510 may be configured to determine if the second risk alert threshold 714 is exceeded at 616. To determine if the second risk alert threshold 714 has been exceeded, the processing circuitry 510 may be configured to determine the health metric delta and compare the health metric delta to the second risk alert threshold 714 in a similar manner as described above. Again, to determine the health metric delta, according to some example embodiments, an average of the health metric parameters 702 may be determined and a difference between the average and the health metric baseline 710 may be taken. This difference may be the health metric delta, which may be compared to the second risk alert threshold 714 (e.g., 10%).

If the health metric delta does not exceed to the second risk alert threshold 714, the detainee health alert device 500 may remain in the first risk state. In the first risk state, the processing circuitry 510 may be configured to control the user interface 550 to have the display 554 and/or the sounder 552 continue to output the first risk alert as described above.

However, if the health metric delta exceeds the second risk alert threshold 714, as indicated at $T_4$, a second risk state may be determined and the processing circuitry 510 may be configured to activate a second risk alert response at 618. In this regard, the processing circuitry 510 may be configured to control the user interface 550 to have the display 554 and/or the sounder 552 to output a second risk alert. According to some example embodiments, the processing circuitry 510 may be configured to control the display 554 to output a red color and/or the sounder 552 to output a periodic tone at a relatively high frequency (i.e., higher than the relatively moderate frequency for the first risk alert). Additionally, the processing circuitry 510 may control the communications interface 540 to transmit a second risk alert communication to the communication interface 416 of the alert device 400 to cause the processing circuitry 410 to control the alert device display 412 and/or the sounder 414 to output a second risk alert. According to some example embodiments, the processing circuitry 410 may be configured to implement the second risk alert by controlling the alert device display 412 to output a red color and/or the sounder 414 to output a periodic tone at a relatively moderate frequency (i.e., higher than the relatively low frequency for the satisfactory alert). Additionally, the second risk alert may also include location data indicating the location of the detainee health alert device 500 and the second risk alert may be transmitted and received by alert devices of medical personnel to prompt the medical personnel to travel to the indicated location to provide medical services.

Figure 8:
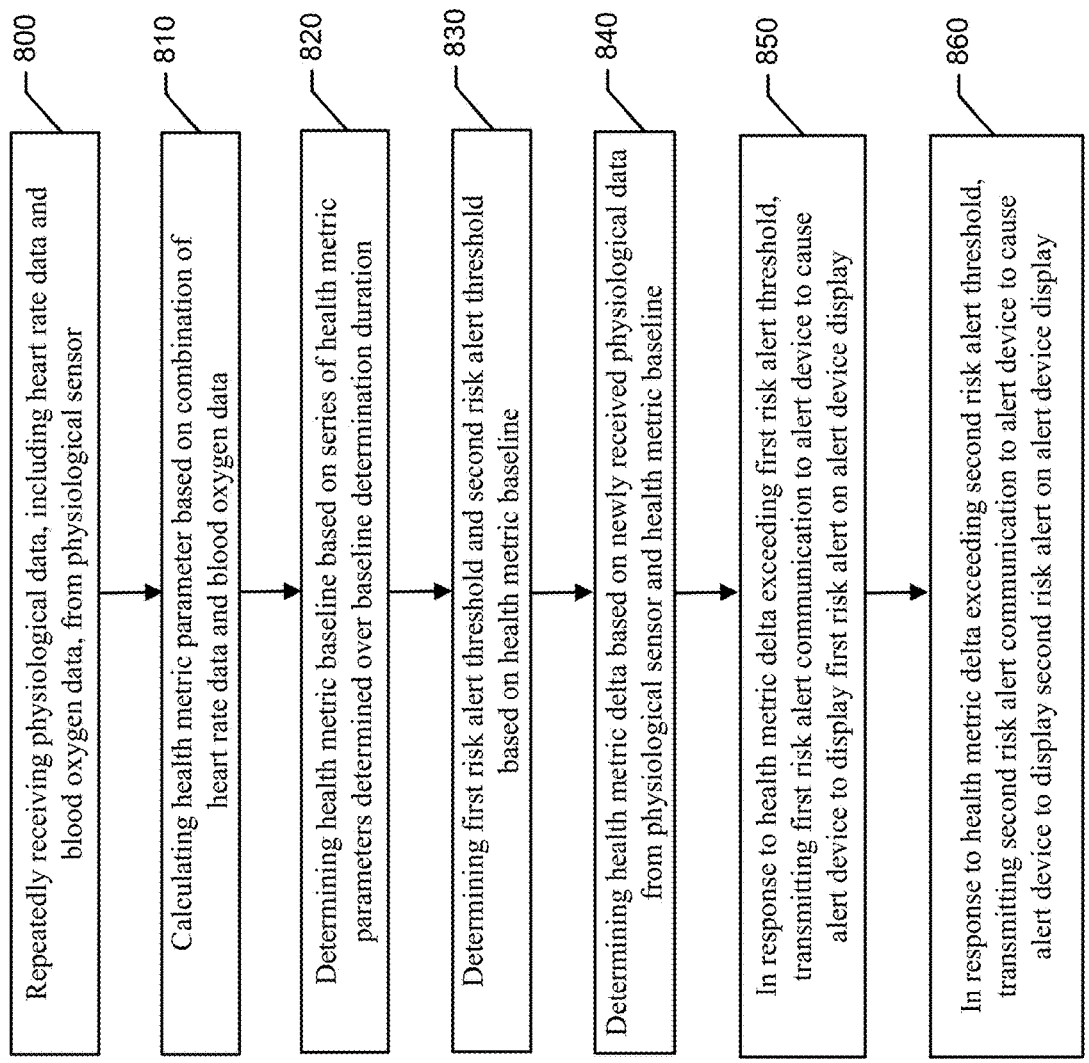
FIG. 8 illustrates a method of operating a detainee health alert device according to some example embodiments.

Now referring to FIG. 8, an example method for generating health risk alert output based on physiological data analysis is provided. According to some example embodiments, the example method may be performed by the detainee health alert device 500, and more specifically the processing circuitry 510 of the detainee health alert device 500. In this regard, the example method may include at 800, repeatedly receiving physiological data from a physiological sensor. The physiological data may include heart rate data and blood oxygen data. The example method may also include, at 810, calculating, e.g., by processing circuitry, a health metric parameter based on a combination of the heart rate data and blood oxygen data, and, at 820, determining, e.g., by the processing circuitry, a health metric baseline based on a series of health metric parameters determined over a baseline determination duration. At 830, the example method may include determining, e.g., by the processing circuitry, a first risk alert threshold and a second risk alert threshold based on the health metric baseline, and, at 840, determining, e.g., by the processing circuitry, a health metric delta based on newly received physiological data from the physiological sensor and the health metric baseline. The example method may also include, at 850, in response to the health metric delta exceeding the first risk alert threshold, transmitting a first risk alert communication to an alert device to cause the alert device to display a first risk alert on the alert device display, and, at 860, in response to the health metric delta exceeding the second risk alert threshold, transmitting a second risk alert communication to the alert device to cause the alert device to display a second risk alert on the alert device display.

According to some embodiments, determining the health metric baseline may include averaging the series of health metric parameters of the baseline determination duration. Additionally or alternatively, according to some example embodiments, the example method may include rendering to a local first risk alert on the local display, in response to the health metric delta exceeding the first risk alert threshold. Additionally or alternatively, according to some example embodiments, the example method may further include controlling a local sounder to emit a sound, in response to the health metric delta exceeding the first risk alert threshold. Additionally or alternatively, according to some example embodiments, the example method may further include transmitting a second risk alert communication to a network entity to notify the network entity of a second risk alert condition of the detainee via the communications interface. Additionally or alternatively, according to some example embodiments, the physiological sensor may be physically coupled to a wrist restraint device such that application of the wrist restraint device to the detainee applies the physiological sensor to the detainee's wrist to sense the physiological data. Additionally or alternatively, according to some example embodiments, the alert device may include a smart phone or a computer. Additionally or alternatively, the physiological sensor may be further configured to capture one or more additional physiological parameters. The one or more additional physiological parameters may include temperature data, blood pressure data, or blood glucose level data. Further, calculating the health metric parameter may include calculating the health metric parameter based on the one or more additional physiological parameters. Additionally or alternatively, according to some example embodiments, the physiological sensor may be further configured to capture temperature data or blood pressure data, and calculating the health metric parameter may include calculating the health metric parameter based on temperature data or blood pressure data. Additionally or alternatively, according to some example embodiments, the example method may further include receiving an applied signal from an application detection sensor, and, in response to receiving the applied signal, activating the physiological sensor to begin capturing the physiological data. Additionally or alternatively, according to some example embodiments, the application detection sensor may be operably coupled to spring device that at least partially wraps around the detainee's wrist when a detainee health alert device is applied to the detainee.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A system comprising:
an alert device comprising an alert device display; and
a detainee health alert device comprising:
  an application detection sensor configured to indicate that detainee health alert device has been applied to a detainee;
  a physiological sensor configured to capture physiological data of the detainee; and
  processing circuitry, wherein the processing circuitry is configured to:
    receive, from the application detection sensor, an indication that the detainee health alert has been applied to the detainee;
    repeatedly receive the physiological data from the physiological sensor, the physiological data comprising physiological data parameters, the physiological data parameters comprising heart rate data and blood oxygen data;
    calculate a health metric parameter based on a combination of the heart rate data and blood oxygen data;
    determine that the health metric parameter has reached steady-state in response to
      a passage of a threshold amount of time since the detainee health alert device has been applied, or
      a slope of a series of health metric parameters is constant relative to one physiological data parameter;

after the health metric parameter has reached steady-state, determine a health metric baseline based on a series of health metric parameters determined over a baseline determination duration that occurs after the health metric parameter has reach steady-state;

determine a first risk alert threshold and a second risk alert threshold based on the health metric baseline;

determine a health metric delta based on newly received physiological data and the health metric baseline;

in response to the health metric delta exceeding the first risk alert threshold, transmit a first risk alert communication to the alert device to cause the alert device to display a first risk alert on the alert device display; and in response to the health metric delta exceeding the second risk alert threshold, transmit a second risk alert communication to the alert device to cause the alert device to display a second risk alert on the alert device display.

2. The system of claim 1, wherein the processing circuitry is further configured to determine the health metric baseline is further configured to average the series of health metric parameters of the baseline determination duration that occurs after the health metric parameter reaches steady-state.

3. The system of claim 1, wherein the detainee health alert device further comprises a local display, and wherein the processing circuitry is further configured to render a local first risk alert on the local display, in response to the health metric delta exceeding the first risk alert threshold.

4. The system of claim 1, wherein the detainee health alert device further comprises a local sounder, and wherein the processing circuitry is further configured to control the local sounder to emit a sound, in response to the health metric delta exceeding the first risk alert threshold.

5. The system of claim 1, wherein the detainee health alert device further comprises a communications interface, and wherein the processing circuitry is further configured to transmit a second risk alert communication to a network entity to notify the network entity of a second risk alert condition of the detainee via the communications interface.

6. The system of claim 1, wherein the physiological sensor is physically coupled to a wrist restraint device that comprises a lockable cuff configured to lock onto and around a wrist of the detainee and restrain movement of the wrist, wherein the physiological sensor is physically coupled such that application of the wrist restraint device to the wrist of the detainee applies the physiological sensor to the wrist of the detainee to sense the physiological data while also restraining movement of the wrist.

7. The system of claim 1, wherein the detainee health alert device further comprises a motion sensor configured to provide motion data;
wherein the processing circuitry is further configured to determine the health metric delta based on the motion data.

8. The system of claim 1, wherein the physiological sensor is further configured to capture one or more additional physiological parameters, the one or more additional physiological parameters comprising temperature data, blood pressure data, or blood glucose level data; and
wherein the processing circuitry is further configured to calculate the health metric parameter based on the one or more additional physiological parameters.

9. The system of claim 1, wherein the detainee health alert device further comprises an application detection sensor configured to detect when the detainee health alert device is applied to the detainee;
wherein the processing circuitry is further configured to:
receive an applied signal from the application detection sensor; and
in response to receiving the applied signal, activate the physiological sensor to begin capturing the physiological data.

10. The system of claim 9, wherein the application detection sensor is operably coupled to a spring device that at least partially wraps around a wrist of the detainee when the detainee health alert device is applied to the detainee.

11. The system of claim 1, wherein the health metric parameter is determined in response to the slope of the series of health metric parameters being constant relative to one physiological data parameter, wherein the slope is a zero slope.

12. A detainee health alert device comprising:
an application detection sensor configured to indicate that detainee health alert device has been applied to a detainee;
a physiological sensor configured to capture physiological data of the detainee; and
processing circuitry configured to:
receive, from the application detection sensor, an indication that the detainee health alert has been applied to the detainee;
repeatedly receive the physiological data from the physiological sensor, the physiological data comprising physiological data parameters, the physiological data parameters comprising heart rate data and blood oxygen data;
calculate a health metric parameter based on a combination of the heart rate data and blood oxygen data;
determine that the health metric parameter has reached steady-state in response to
a passage of a threshold amount of time since the detainee health alert device has been applied, or
a slope of a series of health metric parameters is constant relative to one physiological data parameter;
after the health metric parameter has reached steady-state, determine a health metric baseline based on a series of health metric parameters determined over a baseline determination duration that occurs after the health metric parameter has reach steady-state;
determine a first risk alert threshold and a second risk alert threshold based on the health metric baseline;
determine a health metric delta based on newly received physiological data from the physiological sensor and the health metric baseline;
in response to the health metric delta exceeding the first risk alert threshold, transmit a first risk alert communication to an alert device to cause the alert device to display a first risk alert on an alert device display; and
in response to the health metric delta exceeding the second risk alert threshold, transmit a second risk alert communication to the alert device to cause the alert device to display a second risk alert on the alert device display.

13. The detainee health alert device of claim 12, wherein the processing circuitry is further configured to determine the health metric baseline is further configured to average the series of health metric parameters of the baseline determination duration that occurs after the health metric parameter reaches steady-state.

14. The detainee health alert device of claim 12, further comprising a local display, and wherein the processing circuitry is further configured to render a local first risk alert on the local display, in response to the health metric delta exceeding the first risk alert threshold.

15. The detainee health alert device of claim 12 further comprising a local sounder, and wherein the processing circuitry is further configured to control the local sounder to emit a sound, in response to the health metric delta exceeding the first risk alert threshold.

16. The detainee health alert device of claim 12 further comprising a communications interface, and wherein the processing circuitry is further configured to transmit a second risk alert communication to a network entity to notify the network entity of a second risk alert condition of the detainee via the communications interface.

17. The detainee health alert device of claim 12, wherein the physiological sensor is physically coupled to a wrist restraint device such that application of the wrist restraint device to the detainee applies the physiological sensor to a wrist of the detainee to sense the physiological data.

18. The detainee health alert device of claim 12, wherein the physiological sensor is further configured to capture temperature data or blood pressure data; and
    wherein the processing circuitry is further configured to calculate the health metric parameter based on temperature data or blood pressure data.

19. The detainee health alert device of claim 12 further comprising an application detection sensor configured to detect when the detainee health alert device is applied to the detainee;
    wherein the processing circuitry is further configured to:
        receive an applied signal from the application detection sensor; and
        in response to receiving the applied signal, activate the physiological sensor to begin capturing the physiological data.

20. The detainee health alert device of claim 19, wherein the application detection sensor is operably coupled to spring device that at least partially wraps around a wrist of the detainee when the detainee health alert device is applied to the detainee.

21. A method comprising:
    receiving, from an application detection sensor, an indication that the detainee health alert has been applied to a detainee;
    repeatedly receiving physiological data from a physiological sensor, the physiological data comprising physiological data parameters, the physiological data parameters comprising heart rate data and blood oxygen data;
    calculating, by processing circuitry, a health metric parameter based on a combination of the heart rate data and blood oxygen data;
    determining that the health metric parameter has reached steady-state in response to
        a passage of a threshold amount of time since the detainee health alert device has been applied, or
        a slope of a series of health metric parameters is constant relative to one physiological data parameter;
    after the health metric parameter has reached steady-state, determining, by the processing circuitry, a health metric baseline based on a series of health metric parameters determined over a baseline determination duration that occurs after the health metric parameter has reach steady-state;
    determining, by the processing circuitry, a first risk alert threshold and a second risk alert threshold based on the health metric baseline;
    determining, by the processing circuitry, a health metric delta based on newly received physiological data from the physiological sensor and the health metric baseline;
    in response to the health metric delta exceeding the first risk alert threshold, transmitting a first risk alert communication to an alert device to cause the alert device to display a first risk alert on an alert device display; and
    in response to the health metric delta exceeding the second risk alert threshold, transmitting a second risk alert communication to the alert device to cause the alert device to display a second risk alert on the alert device display.

\* \* \* \* \*